United States Patent
Takeuchi et al.

(10) Patent No.: US 6,939,892 B2
(45) Date of Patent: Sep. 6, 2005

(54) COMPOSITIONS FOR TREATING OR PREVENTING MALARIA AND METHOD OF TREATING MALARIA

(75) Inventors: Tomio Takeuchi, Tokyo (JP); Yusuke Wataya, Okayama (JP); Munekazu Iinuma, Gifu (JP); Hye-Sook Kim, Okayama (JP); Hiroomi Watabe, Yokohama (JP); Hiroshi Naganawa, Tokyo (JP); Yoshikazu Takahashi, Machida (JP)

(73) Assignee: Zaidan Hojin Biseibutsu Kagaku Kenkyu Kai, Tokyo (JP)

( * ) Notice: Subject to any disclaimer, the term of this patent is extended or adjusted under 35 U.S.C. 154(b) by 161 days.

(21) Appl. No.: 10/258,435
(22) PCT Filed: Apr. 26, 2001
(86) PCT No.: PCT/JP01/03619
§ 371 (c)(1), (2), (4) Date: Jan. 27, 2003
(87) PCT Pub. No.: WO01/81339
PCT Pub. Date: Nov. 1, 2001

(65) Prior Publication Data
US 2003/0176492 A1 Sep. 18, 2003

(30) Foreign Application Priority Data
Apr. 26, 2000 (JP) .......................................... 2000-126369

(51) Int. Cl.[7] ...................... A61K 31/35; A61K 31/365
(52) U.S. Cl. ........................................................ 514/451
(58) Field of Search .......................................... 514/451

(56) References Cited

U.S. PATENT DOCUMENTS

| | | | | |
|---|---|---|---|---|
| 4,375,542 A | * | 3/1983 | Waitz et al. ................. 536/7.1 |
| 4,496,549 A | * | 1/1985 | Oronsky ....................... 514/27 |
| 4,536,398 A | * | 8/1985 | Ito et al. ....................... 514/43 |
| 4,551,533 A | * | 11/1985 | Lee et al. ..................... 546/35 |
| 4,578,468 A | * | 3/1986 | Carter et al. ................. 546/35 |
| 4,650,802 A | * | 3/1987 | Kantor et al. ............... 514/279 |
| 4,774,184 A | * | 9/1988 | Lee et al. .................... 435/118 |
| 4,859,598 A | * | 8/1989 | Carter et al. .............. 435/252.1 |
| 4,876,273 A | * | 10/1989 | Hamill et al. ............... 514/451 |
| 5,098,834 A | * | 3/1992 | Hamill et al. ................. 435/74 |

FOREIGN PATENT DOCUMENTS

JP         63192792 A   *   8/1988   ........... C07G/11/00

OTHER PUBLICATIONS

"Tourists Warned About Dangers of Malaria", Jasmina Kuzmanovic, Aug. 16, 19999, Assoicated Press.*
"Factfile on Malaria", May 11, 2004, SpaceDaily.com.*

* cited by examiner

*Primary Examiner*—Vickie Kim
*Assistant Examiner*—Brian S. Kwon
(74) *Attorney, Agent, or Firm*—Stites & Harbison PLLC; B. Aaron Schulman

(57) ABSTRACT

An antibiotic SF2487 substance having the formula (I)

(I)

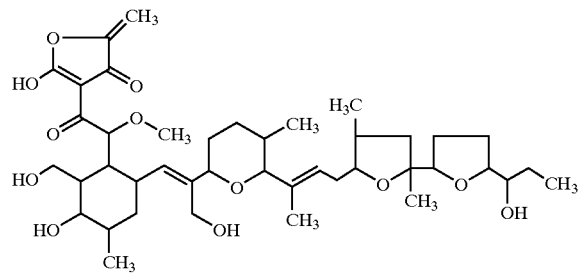

or a salt thereof possesses an antimalarial activity against the proliferation of malarial parasites and is therefore useful as an antimalarial drug.

3 Claims, No Drawings

COMPOSITIONS FOR TREATING OR PREVENTING MALARIA AND METHOD OF TREATING MALARIA

TECHNICAL FIELD

This invention relates to a composition for treating or preventing a malarial disease comprising a known antibiotic SF2487 substance or a salt thereof as an active ingredient. This invention further relates to a method of treating a malarial disease and also a method of preventing a malarial disease in which the antibiotic SF2487 substance or a salt thereof is administrated to a human host as infected with malarial parasites. This invention also relates to a use of the antibiotic SF2487 substance or a salt thereof for the manufacture of antimaralials.

BACKGROUND ART

According to "World Health Report" issued by WHO in 1996, malaria is, like tuberculosis and diphtheria, an infectious disease which once had been considered to have already been overcome, but which is now designated as one of reemerging infections in view of such present situation that there again appear signs of a prevalence of malaria. In 1995, the number of deaths from malaria amounted to 2.1 millions in the world, and presently the number of people as infected with malarial parasites are said to have amounted to 270 millions in total. Areas in which the infection with malaria occurs are not only in the tropics, but also are now spreading, due to the phenomenon of global warming, over the temperate regions, where the malarial infections were rarely found in the past. Even in the Main Island of Japan, there occurs some fear of prevailing malarial diseases in a near future.

The malarial parasites, with which human beings can be infected, include *Plasmodium falciparum*; *Plasmodium vivax*; *Plasmodium malariae*; and *Plasmodium ovate* which belong to *Sporozoea*. Further, there are included those malarial parasites which can infect apes and murines.

Some strains of the malarial parasites have gained a tolerance to a variety of the known antimalarials and thus are difficult to be eliminated. In these circumstances, there have been made extensive investigations for extermination of the malarial diseases, including the development of vaccine, elucidation of ecology and physiology of mosquitoes carrying the malarial diseases, elucidation of physiological mechanism of the malarial parasites, analysis of immune responses of human beings against the malarial parasites, analysis of pathophysiology of malaria, as well as development of new medicines for treating malaria, and so on. In particular, there now occurs a keen demand for developing new antimalarials effective to completely exterminate malaria.

As the medicines currently utilized for treating malaria, there are already known quinine, chloroquine, pyrimethamine, mefloquine, artemisinin, and so on. However, all these known antimalarials are not necessarily deemed to be satisfactory antimalarials since they have poor reliability of their medicinal effects as well as their significant toxicity and side effects against the human beings.

There is further known some polyether-type antibiotics which are produced by microorganisms and which have an antimalarial activity. These antibiotics include monensin and nigericin [refer to Life Sci., Vol.59(20), pp. 309–315 (1996)] as well as salinomycin [refer to Zentralbl. Bakteriol., Mikrobiol. Hyg., Ser. A 256(3), pp. 305–313 (1984)] However, all of monensin, nigericin and salinomycin are of high acute toxicity upon oral administrations of them and also are low and instable in respect of their antimalarial effects, so that they have not yet been utilized in practical applications by now.

There is a further known polyether-type antibiotic, namely SF2487 substance which is disclosed in Japanese Patent No. 1725905 (Japanese Patent Publication Hei-4-13353) to have an anti-microbial activity and an anti-influenza virus activity. This antibiotic SF2487 substance and sodium salt, potassium salt and Ag salt thereof are disclosed also in "The Journal of Antibiotics", Vol. XLIII, No. 3, pp.259–266 (March, 1990), along with its chemical structural formula and the process for the preparation of the SF2487 substance.

DISCLOSURE OF INVENTION

The antibiotic SF2487 substance comprises a tetronic acid moiety as an acidic group in its molecular structure and is therefore markedly different in the chemical structure from monensin, nigericin and salinomycin as mentioned above which each have a carboxylic acid moiety as the acidic group. We, the inventors of the present invention, have presumed that the antibiotic SF2487 substance having the antiviral activity and antibacterial activity will have such pharmacological functions which are different from those of the known antimalarials consisting of polyether-type antibiotics.

Accordingly, we have now carried out such some tests in which the antibiotic SF2487 substance in the form of its sodium salt is reacted with a malarial parasite, *Plasmodium falciparum*, which has infected human red blood cells by incubation in vitro. As a result, we have now succeeded in finding out the fact that the antibiotic SF2487 substance possesses an antimalarial activity inhibitory against the proliferation of *Plasmodium falciparum*. We have now further found that the antibiotic SF2487 substance in the form of sodium salt also can possess an antimalarial activity in vivo against the proliferation of *Plasmodium berghel* which have infected murine red blood cells in vivo, when there are carried out such tests in which the sodium salt of SF2487 substance is intraperitoneally administered to a murine as infected with *Plasmodium berghel*. In consequence, we have found that the antibiotic SF2487 substance or a salt thereof is expectable to be useful as a new antimalarial. Thus, this invention has been completed on the basis of these findings.

According to a first aspect of this invention, therefore, there is provided a composition for treating or preventing a malarial disease, which comprises as an active ingredient an antibiotic SF2487 substance represented by the following formula (I)

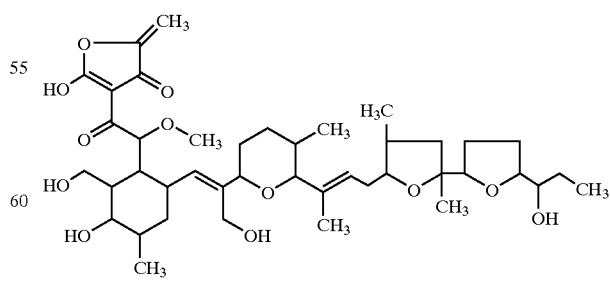

(I)

or a pharmaceutically acceptable salt thereof, in admixture with a pharmaceutically acceptable solid or liquid carrier or carriers.

The known antibiotic SF2487 substance, which is to be contained as an active ingredient in the composition according to the first aspect of this invention, is an acidic substance in the form of colorless crystals having a melting point of 250–252° C. (with decomposition). The antibiotic SF2487 substance may be prepared by cultivating a microbial strain of *Actinomadura* sp. SF2487 strain. A process for the preparation of the antibiotic SF2487 substance and microbiological properties of *Actinomadura* sp. SF2487 strain are described in detail in Japanese Patent Publication Hei-4-13353 specification and also in "The Journal of Antibiotics" Vol. XLIII, No. 3, pp.259–266 (March, 1990) as mentioned above. *Actinomadura* sp. SF2487 strain which is the antibiotic SF2487 substance-producing microorganism has been deposited at National Institute of Bioscience and Human-Technology, National Institute of Advanced Industrial Science and Technology, Ministry of International Trade and Industry, located at 1–3, Higashi 1-chome, Tsukuba-City, Ibaraki Prefecture, Japan, since Mar. 2, 2001, in terms of Budapest Treaty and is accessible under a depository number FERM BP-7474. By the way, *Actinomadura* sp. SF2487 strain was first deposited on Nov. 29, 1986 and had the original depository number FERM P-9063.

The antibiotic SF2487 substance is an acidic substance, and the salts thereof may include pharmaceutically acceptable salts with various metals, for example, alkali metal salts, alkaline earth metal salts and ammonium salt, as well as salts with organic bases, for example, trialkylamine salts (quaternary ammonium salts). By the way, the antibiotic SF2487 substance is a substance identical to the antibiotic A80577 shown in the specification of U.S. Pat. No. 4,876,273 (issued on Oct. 24, 1989).

In the composition for treating or preventing a malarial disease according to this invention, the antibiotic SF2487 substance or a salt thereof may be formulated in the form of a preparation by admixing with a carrier or carriers. Sodium salt of the antibiotic SF2487 substance is soluble in chloroform, ethyl acetate and dimethylsulfoxide, and slightly soluble in ethanol and hardly soluble in water. A carrier which may be incorporated into the composition of this invention may be a pharmaceutically acceptable liquid carrier, for example, glycerine, olive oil, water, physiological saline, ethanol, aqueous ethanol, or may be a solid carrier, for example, lactose, talc, pectin, starch, crystalline cellulose, and so on. The nature and composition of a carrier to be incorporated in the composition may be selected appropriately depending upon the route of administration and the method of administration of the active ingredient.

The composition according to the first aspect of this invention may be formulated in the form of tablets or powder or capsules, when the active ingredient has been mixed with a solid carrier or carriers. When the composition is in the form of a tablet preparation, there may be incorporated therein a binder such as hydroxypropylmethyl cellulose and a lubricant such as magnesium stearate. When the composition is in the form of a solution or suspension preparation dissolved or suspended in an appropriate liquid carrier, the composition may be formulated in the form of an injection preparation. The antibiotic SF2487 substance or a pharmaceutically acceptable salt thereof may be administered either orally or parenterally, for example, by intravenous, subcutaneous, intrarectal or intraperitoneal injection. The proportion of the antibiotic SF2487 substance or a salt thereof contained in the oral or parenteral preparations may be, for example, in a range of 0.01–90%, preferably in a range of 0.1–70%, based on the weight of the composition, with the balance being the carrier or auxiliary agent.

The dosage of SF2487 substance may be decided, with taking various conditions into consideration, such that the total dosage of the SF2487 substance as given in continuous or intermittent administrations does not exceed a certain limit. Normally, the dosage for adult may be in a range of 0.1–1,000 mg/kg /day, preferably in a range of 0.5–500 mg/kg/day. It is a matter of course that a particular dosage of the SF2487 substance may vary depending upon various factors, for example, method of administration, conditions of patient or host to be treated, such as age, body weight, sex, sensitivity, food, time of administration, medicine to be administered concurrently, degree of the patient or degree of malarial disease of the patient. The appropriate dose and times of administration of the SF2487 substance under certain conditions may be decided through preliminary tests for determining an optimal dose, by a medical specialist in account of the above-mentioned guideline.

Further, according to a second aspect of this invention, there is provided a method for treating a malarial disease, which comprises administering orally or parenterally to a human host having been infected with the malarial parasites and having a symptom of the malarial disease, the antibiotic SF2487 substance of the formula (I)

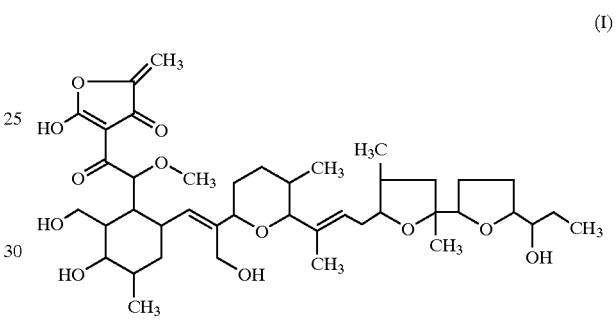

(I)

or a pharmaceutically acceptable salt thereof, at a dosage effective and sufficient to inhibit the proliferation of malarial parasites which are present in the red blood cells in the human host.

In the method for treating a malarial disease according to the second aspect of this invention, it is preferred that the antibiotic SF2487 substance or sodium or potassium salt thereof is administered to the human host orally or intravenously, subcutaneously or intrarectally at a dosage of 0.1–1000 mg/kg, preferably at a dosage of 0.5–500 mg/kg.

Furthermore, according to a third aspect of this invention, there is provided a method for preventing a malarial disease, which comprises administering orally or parenterally to a human host having been infected with the malarial parasites but having not yet shown any symptom of the malarial disease, the antibiotic SF2487 substance of the formula (I)

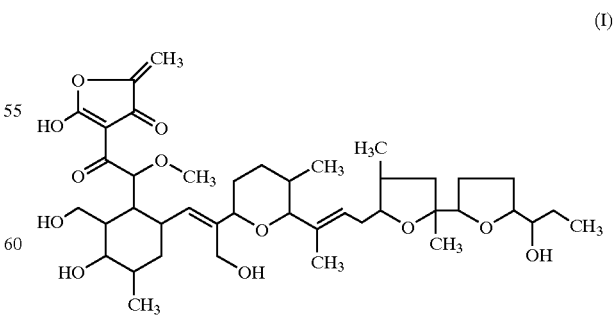

(I)

or a pharmaceutically acceptable salt thereof, at a dosage effective and sufficient to inhibit the proliferation of the malarial parasites in the human host.

In the method for preventing a malarial disease according to the third aspect of this invention, it is preferred that the antibiotic SF2487 substance or sodium or potassium salt thereof is administered to the human host orally or intravenously, subcutaneously or intrarectally at a dosage of 0.1–1000 mg/kg, preferably at a dosage of 0.5–500 mg/kg.

Yet further, according to a fourth aspect of this invention, there is provided a use of the antibiotic SF2487 of the formula (I)

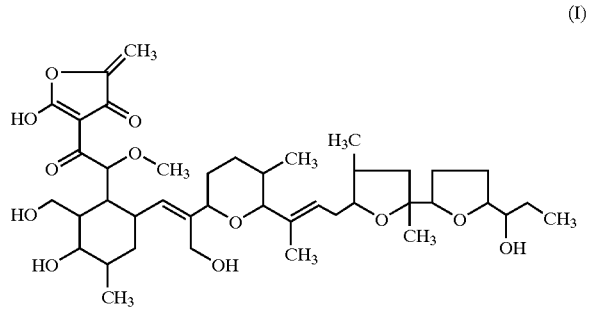

(I)

or a pharmaceutically acceptable salt thereof, for the manufacture of an antimalarial drug. It is here preferred that the use in made of a sodium salt of the antibiotic SF2487 substance of formula (I).

BEST MODE FOR CARRYING OUT THE INVENTION

Examples of some preparations of the composition according to the first aspect of this invention are illustrated in the following Examples 1–2.

EXAMPLE 1

Tablets

The ingredients as indicated below were mixed together in appropriate proportions, and the resulting mixture was formulated into the form of tablets by a conventional method for tableting by compression. There could be obtained tablets each weighing 280 mg. The composition of each tablet was shown in the following.

| | |
|---|---|
| SF2487 substance Na salt (active ingredient) | 100 mg |
| Hydroxypropylmethyl cellulose (binder) | 6 mg |
| Lactose (excipient) | 120 mg |
| Sodium crosscarmelose (disintegrator) | 50 mg |
| Magnesium stearate (lubricant) | 4 mg |
| Total | 280 mg |

EXAMPLE 2

Tablets

The ingredients as indicated below were mixed together in appropriate proportions, and the resulting mixture was formulated into the form of tablets by a conventional method for tableting by compression. There could be obtained tablets each weighing 300 mg. The composition of each tablet was shown in the following.

| | |
|---|---|
| SF2487 substance Na salt (active ingredient) | 100 mg |
| Hydroxypropyl cellulose Type L (binder) | 5 mg |
| Corn starch (excipient) | 60 mg |
| Crystalline cellulose (excipient) | 80 mg |
| Carboxymethyl starch Na salt (disintegrator) | 50 mg |
| Magnesium stearate (lubricant) | 5 mg |
| Total | 300 mg |

Now, the antimalarial activity of the antibiotic SF2487 substance to be used as the active ingredient in this invention is illustrated by Test Examples 1–2.

Test Example 1

"In Vitro" Test of the Inhibitory Activity Against Malarial Parasites

In this test Example, there were carried out, in parallel, determinations of the antimalarial activity against malarial parasites and also determinations of toxicity of the antibiotic SF2487 substance (sodium salt) and of each of comparative compounds under test (such as quinine, chloroquine, pyrimethamine, mefloquine, and others). Further, there was estimated the ratio of the antimalarial activity of each test compound against malarial parasites to the toxicity of each test compound. And, from the so estimated ratio, it was evaluated whether each test compound has a usefulness as an antimalarial drug.

1. Preparation of a Culture of Malarial Parasite, *Plasmodium falciparum*

In this test Example, two strains of *Plasmodium falciparum*, namely strain FCR-3 (ATCC 30932) and strain Honduras-1 (ATCC 30950) were used as the malarial parasites to be tested, and each malarial strain was incubated separately in vitro as described below. The culture medium to be used for the incubation of the malarial parasites under test was prepared by filtering and sterilizing the PRMI 1640 medium, adjusting the pH thereof to 7.4, followed by supplementing with a volume of human serum containing human red blood cells so that the culture medium had a serum concentration of 10% (by weight). The resulting culture medium as supplemented with the human serum was then adjusted to have a hematocrit level (namely, a ratio of the total volume of the red blood cells to the volume of the liquid culture medium comprising the suspended red blood cells) of 5%, and thereafter the culture medium as adjusted was placed in individual wells of 24-well incubation microplates. The culture medium in each well was inoculated with *Plasmodium falciparum* under test. The initial rate (%) of infection of the red blood cells with the malarial parasite in individual wells was then adjusted to a value of 0.1% at the start of the incubation. Thereafter, there was carried out the incubation of the red blood cells along with the infecting *Plasmodium falciparum*. This incubation was effected at 36.5° C. in an atmosphere comprising 5.0% oxygen, 5.0% carbon dioxide and 90% nitrogen.

The culture medium present in each well was daily changed freshly. At the time when the rate (%) of infection of the red blood cells with the malarial parasite increased to reach a value of 4%, the transfer of the incubated cultures to another incubation microplates was conducted. Thus, the cultures of the malarial parasites under test were prepared.

By the way, the rate (%) of infection of the red blood cells with the malarial parasite as above-mentioned was evaluated by a procedure that comprised removing a sample from the culture of the parasitized red blood cells in each well, preparing thin blood film specimen containing the red blood cells from each sample, staining said thin blood film specimen by means of Giemsa staining or Diff-Qick staining method, counting the number of the stained red blood cells as infected with the malarial parasite per one thin blood film, under a microscope (oil immersion; 1,000×), and calculating the rate (%) of infection of the red blood cells with malarial parasite according to the undermentioned equation:

$$\text{Rate (\%) of infection of red blood cells with malarial parasite} = \frac{\begin{pmatrix}\text{Counted number of red blood} \\ \text{cells as infected with} \\ \text{malarial parasite}\end{pmatrix}}{\begin{pmatrix}\text{Total number of red blood} \\ \text{cells under test}\end{pmatrix}} \times 100$$

In turn, the abovementioned culture of the parasitized red blood cells as prepared in the above was subjected to a centrifugation to collect the red blood cells which had been infected with the malarial parasite. The infected red blood cells so collected were washed with an PRMI 1640 medium supplemented with the human serum, and then were added with such red blood cells which were not yet infected with the malarial parasite. Thus, there was prepared such a culture of the malarial parasite having infected the red blood cells, in which the initial rate (%) of infection of the red blood cells with the malarial parasite had firstly been adjusted to a value of 0.3%. The hematocrit level of this culture of the malarial parasite so prepared at this time point was 3%.

On the other hand, the compound to be tested in the present experiments was previously prepared in the form of a solution of each compound dissolved in a sterilized water, dimethylformamide (DMF) or dimethylsulfoxide (DMSO).

2. Test for Assay of the Antimalarial Activity of Test Compound Inhibitory to the Proliferation of Malarial Parasites (i) The culture medium to be used for incubation of malarial parasite as above-mentioned was placed in individual wells of a multidish 24-wells. Then, for the treated test groups, each solution of the test compound as previously prepared in the above was added in an amount of 5 to 10 microliters ($\mu$l) into each well containing said culture medium therein. Then, the concentration of the test compound as added to the culture medium present in the individual wells of the multidish 24-well microplates was adjusted to different values in the individual wells. The test was carried out in duplicate or triplicate. On the other hand, for the control test groups (untreated), no test compound was added to each well, but instead thereof sterilized water, DMF or DMSO was added thereto in an amount of 10 $\mu$l.

After that, the culture of malarial parasite as already prepared in the above (having the initial rate (%) of infection of red blood cells of 0.3%) was added in an amount of 990 to 995 $\mu$l by a pipetting into each well of the treated test groups and of the control test groups. The pipetting was effected carefully and gently so that the red blood cells as infected with the malarial parasite and the red blood cells not infected with the malarial parasite were evenly suspended in the culture medium within each well.

(ii) Into an incubator were placed the multidish 24-well microplates, which had the individual wells each having contained the culture medium and the culture of the malarial parasite along with or without the test compound added (thus, said microplates had the wells of the treated test groups and the wells of the control test groups). The microplates so placed in the incubator were incubated at 36.5° C. for 72 hours in an atmosphere comprising 5.0% oxygen, 5.0% carbon dioxide and 90% nitrogen. Thereafter, each sample of the cultures so incubated was removed from the cultures so incubated in the individual wells of the treated test groups and of the control test groups (untreated). From each sample, there was prepared a thin blood film specimen containing the red blood cells under test.

The red blood cells present in each thin blood film specimen so prepared were stained and then were examined under a microscope to count the number of the parasitized red blood cells as infected with malarial parasite. Similarly to the abovementioned procedure, and according to the abovementioned equation, there were evaluated the rates (%) of infection of red blood cells with malarial parasite for the test groups as treated with SF2487 substance (Na salt) and also for the test groups as treated with a comparative compound tested, and there was evaluated the rate (%) of infection of red blood cells with malarial parasite for the control test groups (untreated).

Then, the rate (%) of proliferation of malarial parasites, which is defined by the undermentioned equation, is calculated from the values of the rate (%) of infection of red blood cells with malarial parasite as evaluated in the above.

$$\text{Rate (\%) of proliferation of malarial parasites} = \frac{(b-a)}{(c-a)} \times 100$$

In the equation above which was used to calculate the aforesaid rate (%) of proliferation of malarial parasite, "a" means the value of the rate (%) of infection of red blood cells with malarial parasite within the culture medium present at the time when the test for the incubation of malarial parasite was just started, that is, when the previously prepared culture of malarial parasite was just added to the culture medium in each well (thus, the value of "a" was equal to 0.3% at which the initial rate (%) of infection of the inoculating culture of malarial parasite had been adjusted). Besides, "b" means the value of the rate (%) of infection of red blood cells with malarial parasite after the incubation of malarial parasite had been carried out in the presence of a test compound for 72 hours in the wells of the treated test groups which had contained the culture medium containing the test compound added, and "c" means the value of the rate (%) of infection of red blood cells with malarial parasite after the incubation of malarial parasite had been carried out in the absence of any test compound for 72 hours in the wells of the control test groups (untreated) which had contained the culture medium containing only the solvent added without the test compound. Therefore, the value of the equation (c-a) indicates a degree of the proliferation of malarial parasite when incubated in the absence of the test compound, whereas the value of the equation (b-a) indicates a degree of the proliferation of malarial parasite when incubated in the presence of the test compound added.

The results of the mean of the above duplicate or triplicate tests of measurements of the rates (%) of proliferation of malarial parasite upon the use and presence of the antibiotic SF2487 substance (Na salt) according to this invention and also upon the use and presence of chloroquine as one example of the comparative compounds (namely, known antimalarial drugs), which were carried out by the abovementioned experimental procedures, are shown in Table 1 below.

TABLE 1

| Concentration of test compound added to the culture medium (Molar) | Rate (%) of proliferation of malarial parasite | |
|---|---|---|
| | SF2487 substance (Na salt) (according to this invention) | Chloroquine (comparative compound) |
| $1 \times 10^{-10}$ | 100 | |
| $3 \times 10^{-10}$ | 100 | |
| $7 \times 10^{-10}$ | 85 | |
| $1 \times 10^{-9}$ | 60 | 100 |
| $3 \times 10^{-9}$ | 40 | 100 |
| $7 \times 10^{-9}$ | 25 | 72 |
| $1 \times 10^{-8}$ | 10 | 56 |
| $3 \times 10^{-8}$ | 5 | 45 |
| $7 \times 10^{-8}$ | 0 | 35 |
| $1 \times 10^{-7}$ | 0 | 5 |
| $1 \times 10^{-6}$ | | 0 |

It may be estimated from the results of Table 1 that the value of the concentration of SF2487 substance Na salt, which is necessary to inhibit the proliferation (i.e. the increase in the parasite density) of malarial parasite by 50% (that is, the concentration for the 50% inhibition, $EC_{50}$) in the treated test group, on the basis of the rate (%) of the proliferation of malarial parasite effected in the control test group, is to be $2 \times 10^{-9}$ M., with taking such assumption that the value of the rate (%) of the proliferation of malarial parasite effected in the control test group (untreated) of incubating the malarial parasite in the absence of any test compound would be 100%.

3. Determination of Toxicity of the Test Compound Against Subclone F28-7 Cells of FM3A Cell Line Originating From a Mouse Mammary Tumor Cells of subclone F28-7 cell line of a mouse mammary tumor, which is a wild type cell line of the FM3A cell line originating from a mouse mammary tumor, were used as the test cells. The culture medium to be used for cultivation of the cells of the subclone F28-7 cell line was prepared by supplementing an ES medium with 2% of a heat-inactivated fetal bovine serum. The cultivation of the subclone F28-7 cell line under test was effected in this serum-supplemented ES medium at 37° C. in air containing 5% $CO_2$. The doubling time which was required for the number of cells of the subclone F28-7 cell line to increase twice-folds under these conditions of the cultivation was about 12 hours.

After the pre-cultivation was effected, the cell density of cells of the subclone F28-7 cell line which had entered the logarithmic proliferation phase was adjusted to a level of $5 \times 10^4$ cells/ml by diluting the culture of the cells with a volume of the fresh culture medium. Thus, there was prepared a cell suspension of cells of the subclone F28-7 cell line as cultured.

For the solution of the test compound, there was used the same solution as that which was hereinbefore prepared in the test for the determination of the antimalarial activity of the test compound against the proliferation of malarial parasite.

The culture medium to be used for the cultivation of the subclone F28-7 cell line above mentioned was placed in the individual wells of a multidish 24-wells. Then, for the treated test groups, the solution of the test compound was added in an amount of 5~10 microliters to the culture medium in each well of the incubation plate so as to adjust a final concentration of the test compound as added to be $1 \times 10^{-4}$ to $1 \times 10^{-6}$ M.

The test was carried out in duplicate or triplicate. On the other hand, for the control test groups (untreated), no test compound was added to each well, but instead thereof a sterilized water, DMF or DMSO was added to each well in an amount of 10 μl. Then, the cell suspension of cells of the subclone F28-7 cell line as already prepared in the above was dispensed in an amount of 990–995 μl to each well by pipetting. The pipetting was effected carefully and gently, so that the cells as added were evenly suspended in the culture medium in each well. Thereafter, the cells of subclone F28-7 cell line were incubated for 48 hours under the aforesaid cultivating conditions. Then, the number of the cells of the subclone F28-7 cell line was counted by means of a microcell counter (CC-108, Toa Medical Electric Co.) for the cell culture as obtained in the individual wells of both the treated test groups and the control test (untreated) groups.

The inhibitory activity of the test compound against the proliferation of cells of the subclone F28-7 cell line was subsequently estimated from such value of the rate (%) of the proliferation of cells of the subclone F28-7 cell line which is defined by the undermentioned equation with reference to the counted number of cells of the subclone F28-7 cell line in the cell culture contained in each well and having been incubated in the presence of the test compound added for the treated test group, and with reference to the counted number of cells of the subclone F28-7 cell line having been incubated in the absence of the test compound for the control test group. The toxicity of the test compound was thus evaluated from the value of the rate (%) of proliferation of cells of the subclone F28-7 cell line so estimated.

$$\text{Rate (\%) of proliferation of cells of the subclone F28-7} = \frac{(C-A)}{(B-A)} \times 100$$

In the above equation, "A" means the counted number of cells of the subclone F28-7 cell line contained in each well of both of the treated test group and the control test group at the start of the cell incubation; and "B" means the counted number of cells of the subclone F28-7 cell line contained in the well of the control test group (untreated) and having been incubated in the absence of the test compound after the cell incubation was effected for 48 hours; but "C" means the counted number of cells of the subclone F28-7 cell line contained in the well of the treated test group and having been incubated in the presence of the test compound after the cell incubation was effected for 48 hours. Therefore, the value of the equation (B-A) indicates a degree of proliferation of cells of the subclone F28-7 cell line as incubated in the absence of the test compound, whereas the value of the equation (C-A) indicates a degree of proliferation of cells of the subclone F28-7 cell line as incubated in the presence of the test compound. The numerical data of the so estimated mean values of the rate (%) of the proliferation of cells of the F28-7 cell line as incubated in the presence of SF2487 substance under test, in comparison with the numerical data for the comparative test group as treated with chloroquine (a comparative medicine), are shown in Table 2 below.

TABLE 2

| Concentration of test compound added to the culture medium (Molar) | Rate (%) of proliferation of cells of the F28-7 cell line | |
|---|---|---|
| | SF2487 substance Na salt (according to this invention) | Chloroquine (comparative compound) |
| $1 \times 10^{-7}$ | 100 | |
| $3 \times 10^{-7}$ | 100 | |
| $7 \times 10^{-7}$ | 70 | |
| $1 \times 10^{-6}$ | 58 | 100 |
| $3 \times 10^{-6}$ | 45 | 100 |
| $7 \times 10^{-6}$ | 10 | 100 |
| $1 \times 10^{-5}$ | 0 | 80 |
| $3 + 10^{-5}$ | 0 | 52 |
| $7 \times 10^{-5}$ | | 39 |
| $1 \times 10^{-4}$ | | 0 |
| $3 \times 10^{-4}$ | | 0 |

It may be estimated from the results of Table 2 that such value of the concentration of SF2487 substance Na salt, which is necessary to inhibit the proliferation of cells of the F28-7 cell line by 50% (the concentration for the 50% inhibition, $EC_{50}$) in the treated test group, on the basis of the rate (%) of the proliferation of the same cells as effected in the control test group, is to be $1.6 \times 10^{-6}$ M., with taking such assumption that the rate (%) of the proliferation of cells of the F28-7 cell line as effected in the control test group (untreated) of cultivating the cells of the F28-7 cell line in the absence of any test compound would be 100%.

4. Estimation of Practical Utilizability of the Test Compound for an Antimalarial Drug In general, if a compound exhibits a high antimalarial activity against the proliferation of malarial parasites, but can have a high toxicity against cells of human beings (for example, a cell line of the above-mentioned mouse mammary tumor which is representative of human cell line), it is necessary that the administration of said compound to human beings as an antimalarial drug is practically restricted, or the dosage of said compound as administered is limited to be a low extent, resulting in that the practical utilizability of said compound as an antimalarial drug must be estimated to be poor.

The practical utilizability in the above sense of the compounds tested in this Test Example as an antimalarial drug has now been estimated with making reference to such selective toxicity of said test compounds which may be evaluated from the undermentioned equation for estimating a balance that intervenes between the inhibitory activity of the test compound against malarial parasites and the toxicity of the same test compound against human cells.

First of all, there was determined the value of the rate (%) of infection of human red blood cells with the malarial parasite in the control test group (untreated) where the malarial parasite was cultivated in a culture medium for cultivating the malarial parasite without addition of the test compound thereto. It was then assumed that the value of the rate (%) of the infection of human red blood cells with the parasite so determined for the control test group would be 100%. With taking this assumption, the test for the treated test group was carried out in such way that the test compound was added to the culture medium for cultivating the malarial parasite, followed by cultivating the malarial parasite in said culture medium in the presence of the added test compound, and in such way that evaluation was then made of such value of the concentration of the test compound (expressed in molar concentration) which was necessary to inhibit by 50% the rate (%) of the proliferation of the malarial parasite effected in said control test group. The value of the molar concentration so evaluated of the test compound to achieve the 50% inhibition of the proliferation of the malarial parasite was defined to be $EC_{50}$ value of the test compound for the malarial parasite.

In a next determination, cells of the F28-7 cell line were incubated in the culture medium containing no test compound therein, for the control test group. The value of the rate (%) of proliferation of cells of the F28-7 cell line so effected in this control test group would be assumed as 100%. With taking this assumption, the test for the treated test group was carried out in such way that the test compound was added to the culture medium, followed by incubating the cells of the F28-7 cell line in said culture medium in the presence of the added test compound, and in such way that evaluation was then made of such value of the concentration of the test compound (expressed in molar concentration) which was necessary to inhibit by 50% the rate (%) of the proliferation of cells of the F28-7 cell line effected in the control test group. The value of the molar concentration so evaluated of the test compound to achieve the 50% inhibition of the proliferation of the F28-7 cell line was defined to be $EC_{50}$ value of the test compound for the F28-7 cell line. With using these two $EC_{50}$ values so evaluated, there is estimated the selective toxicity of the test compound, which is defined by the following equation:

$$\text{Value of selective toxicity of a test compound} = \frac{\left(\begin{array}{c} EC_{50} \text{ value of test compound} \\ \text{for cells of the F28-7} \\ \text{cell line} \end{array}\right)}{\left(\begin{array}{c} EC_{50} \text{ value of test compound} \\ \text{for malarial parasite,} \\ \text{Plasmodium falciparum} \end{array}\right)}$$

Table 3 given below shows the results of the $EC_{50}$ values so evaluated and the values of the selective toxicity estimated as above for some known antimalarial drugs tested and for the antibiotic SF2487 substance.

TABLE 3

| | $EC_{50}$ values, namely molar concentrations of test compound for the 50% inhibition of proliferation | | |
|---|---|---|---|
| Test compound | P. falciparum FCR-3 strain | the F28-7 cell line | Selective toxicity |
| Quinine (comparative) | $1.1 \times 10^{-7}$ | $1.0 \times 10^{-4}$ | 910 |
| Chloroquine (comparative) | $1.8 \times 10^{-8}$ | $3.2 \times 10^{-5}$ | 1780 |
| Pyrimethamine (comparative) | $1.0 \times 10^{-9}$ | $1.2 \times 10^{-7}$ | 120 |
| Mefloquine (comparative) | $3.2 \times 10^{-8}$ | $2.9 \times 10^{-6}$ | 91 |
| Artemisinin (comparative) | $7.8 \times 10^{-9}$ | $1.0 \times 10^{-5}$ | 1280 |
| SF2487 substance Na salt (this invention) | $2.0 \times 10^{-9}$ | $1.6 \times 10^{-6}$ | 800 |

Test Example 2

"In Vivo" Test of Antimalarial Activity Against Malarial Parasite

1. Mice and Malarial Parasite Used

As mice for this test, there were used ICR mice (male) of 5-weeks old with body weight of 26–31 g (five mice per group). As the source of the malarial infection for this experiment, murine malarial parasite, *Plasmodium berghei* NK65 strain was used. This malarial parasite is known as such a virulent strain that mice, if infected with this particular parasite, die out completely due to an abrupt proliferation of the parasite.

2. Test Procedure

Blood sample was drawn by cardiac puncture from each of the donor ICR mice which had been infected with *Plasmodium berghei* NK65 strain. With the blood sample drawn, the rate (%) of infection of the red blood cells with this murine malarial parasite was measured and evaluated in accordance with the equation hereinbefore given in Test Example 1. Then, the cell suspension of the parasitized red blood cells of the said blood sample was diluted with a volume of the murine serum to adjust the density of the malarial parasites to be $1 \times 10^6$ parasites/ml, and 0.2 ml of the cell suspension of the parasitized red blood cells so adjusted was intravenously injected at the tail vein of each of the recipient mice which were not yet infected with the malarial parasite.

For sake of convenience, a time schedule was so set that the time of inoculating the test mice with the malarial parasite by intravenous injection of the cell suspension of the parasitized red blood cells was Day 0. On the basis of this time schedule, at the lapse of 2 hours from the time of said parasite inoculation and on Day 1, a solution of the test compound dissolved in DMSO (100 µl) was intraperitoneally administered once a day to each of the test mice at different doses. On the Day 4, a volume of blood sample was drawn at the tail vein of each test mouse, and a thin blood film specimen of the blood sample was prepared. The red blood cells in the thin blood film specimen as prepared were examined under a microscope. For both of the untreated test group and the treated test group, the rate (%) of infection of the red blood cells with the malarial parasite in each of the mouse blood samples was evaluated. From the results of these tests, it was found that the antibiotic SF2487 substance (Na salt), when administered by intravenous injection at a dose of 5 mg/kg, can give a value of 80% for the rate (%) of inhibition against the proliferation of the malarial parasite. The rate (%) of inhibition against the proliferation of the malarial parasite used here indicates such value as calculated by the following equation:

$$\text{Rate (\%) of inhibition against the proliferation of malarial parasite} = \left(1 - \frac{B}{A}\right) \times 100$$

where A means the average rate (%) of infection of the red blood cells with the malarial parasite as effected in the untreated test group, and B means the average rate (%) of infection of the red blood cells with the malarial parasite as effected in the treated test group.

Test Example 3

Acute Toxicity

SF2487 substance (Na salt) in the form of a solution dissolved in a physiological saline containing 10% DMSO was administered to ICR mice (5-weeks old, 3 mice per group) in different doses by intraperitoneal injection. On the 14th day from the administration, one mouse died among three mice in the mice group having administration of 25 mg/kg of SF2487 substance (Na salt), whereas all three mice survived in the mice group having administration of 12.5 mg/kg of SF2487 substance (Na salt). In these tests for the intraperitoneal administration, the $LD_{50}$ value of SF2487 substance (Na salt) was found to be 25 mg/kg or higher.

INDUSTRIAL APPLICABILITY

It has been found, according to this invention, that antibiotic SF2487 substance or a salt thereof possesses an inhibitory activity against the proliferation of malarial parasites and therefore is useful as a drug for treating or preventing a malarial disease.

What is claimed is:

1. A method for treating malaria, which comprises administering orally or parenterally an antibiotic SF2487 of the formula (I)

(I)

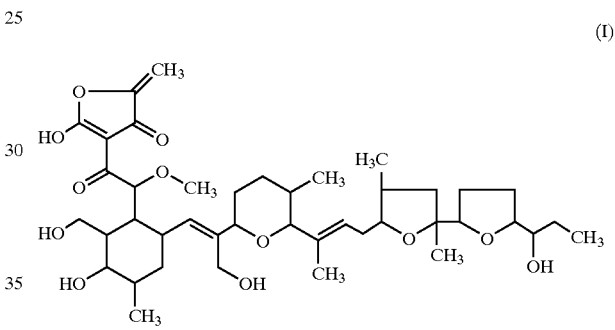

or a pharmaceutically acceptable salt thereof, to a human host having been infected with the malarial parasites and having symptoms of malaria, at a dosage effective and sufficient to inhibit the proliferation of the malarial parasites which are present in the red blood cells in the human host.

2. The method as claimed in claim 1, wherein the antibiotic SF2487 or sodium salt or potassium salt thereof is administered orally, intravenously, subcutaneously or intrarectally, to the human host at a dosage of 0.1–1000 mg/kg.

3. The method according to claim 2 wherein the dosage is 0.5–500 mg/kg.

* * * * *

UNITED STATES PATENT AND TRADEMARK OFFICE
CERTIFICATE OF CORRECTION

PATENT NO. : 6,939,892 B2
APPLICATION NO. : 10/258435
DATED : September 6, 2005
INVENTOR(S) : Takeuchi et al.

It is certified that error appears in the above-identified patent and that said Letters Patent is hereby corrected as shown below:

On the Title page, item (73) should be corrected to include the second Assignee as follows:

-- (73) Assignees: Zaidan Hojin Biseibutsu Kagaku Kenkyu Kai, Tokyo (JP); Meiji Seika Kaisha, Ltd., Tokyo, (JP) --

Signed and Sealed this

Fifteenth Day of August, 2006

JON W. DUDAS
*Director of the United States Patent and Trademark Office*